United States Patent [19]

Lantzsch et al.

[11] Patent Number: 4,987,251

[45] Date of Patent: Jan. 22, 1991

[54] PROCESS FOR THE PREPARATION OF TRANS-2,2-DIMETHYL-3-(2,2-DICHLOROVINYL)-CYCLOPROPANECARBOXYLIC ACID

[75] Inventors: Reinhard Lantzsch, Wuppertal, Fed. Rep. of Germany; Karl Steinbeck, Leawood, Kans.

[73] Assignee: Bayer Aktiengesellschaft, Leverkusen, Fed. Rep. of Germany

[21] Appl. No.: 422,840

[22] Filed: Oct. 17, 1989

Related U.S. Application Data

[63] Continuation of Ser. No. 180,410, Apr. 12, 1988, abandoned.

[30] Foreign Application Priority Data

Apr. 16, 1987 [DE] Fed. Rep. of Germany ....... 3712988

[51] Int. Cl.$^5$ .............................................. C07C 61/04
[52] U.S. Cl. ..................................................... 562/506
[58] Field of Search ......................................... 562/506

[56] References Cited

U.S. PATENT DOCUMENTS 4,423,243 12/1983 Jaut et al. ............................ 560/124

FOREIGN PATENT DOCUMENTS 0095047 11/1983 European Pat. Off. .
0095696 12/1983 European Pat. Off. .
3100354 8/1982 Fed. Rep. of Germany .
3216723 11/1983 Fed. Rep. of Germany .
3231814 3/1984 Fed. Rep. of Germany .

*Primary Examiner*—Michael L. Shippen
*Attorney, Agent, or Firm*—Sprung Horn Kramer & Woods

[57] ABSTRACT

A process for the preparation of trans-2,2-di-methyl-3-(2,2-dichlorovinyl)-cyclopropanecarboxylic acid of the formula (I)

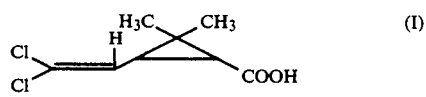

comprising reacting a chloroketone of the formula (II)

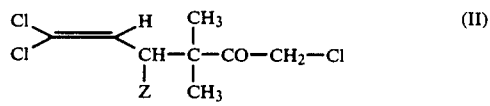

in which
Z represents chlorine or bromine,
with an aqueous solution of an alkali metal hydroxide.

6 Claims, No Drawings

PROCESS FOR THE PREPARATION OF TRANS-2,2-DIMETHYL-3-(2,2-DICHLOROVINYL)-CYCLOPROPANECARBOXYLIC ACID

This is a continuation of application Ser. No. 180,410, filed Apr. 12, 1988, now abandoned.

The present invention relates to a new process for the preparation of trans-2,2-dimethyl-3-(2,2-dichlorovinyl)-cyclopropanecarboxylic acid (=trans-permethric acid). Trans-permethric acid is a useful intermediate for the preparation of insecticidally active pyrethroids.

It is already known that cis/trans mixtures of 3-vinyl-substituted 2,2-dimethylcyclopropane-1-carboxylic acids are obtained when polyhalogenoalkanes are added onto 1-chloro-3,3-dimethyl-pent-4-en-2-one and the halogenoketone mixture obtainable therefrom is further reacted with bases.

A considerable amount of undesired cis-acids is obtained in this process (compare DE-OS (German Published Specification) 3,100,354).

It is also known that trans-3-vinyl-substituted 2,2-dimethylcyclopropane-1-carboxylic acids are obtained when 4,4-dimethyl-6-bromo-3-halogeno-1-hexen-5-ones are reacted with bases at elevated temperatures(compare DE-OS (German Published Specification) 3,216,723, DE-OS (German Published Specification) 3,231,814 and European Published Specification 095,047). The purity of the trans-acids formed in this process is particularly unsatisfactory since it is carried out at elevated temperatures.

It is furthermore known that the metering direction has an influence on the isomer ratio of 3-vinyl-substituted 2,2-dimethyl-cyclopropanecarboxylic acids. However, the formation of cis-acids also cannot be excluded completely in this process.

It has now been found that very pure trans-2,2-dimethyl-3-(2,2-dichlorovinyl)-cyclopropanecarboxylic acid of the formula (I)

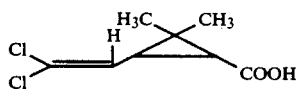

is obtained by a process in which chloroketones of the formula (II)

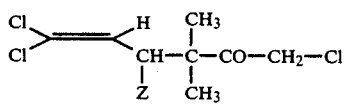

in which
Z represents chlorine or bromine,
are reacted with an aqueous solution of alkali metal hydroxide, in particular sodium hydroxide and/or potassium hydroxide.

The reaction is to be described as surprising, since the adduct mixture of 1,4,6,6,6-pentachloro- 3,3-dimethyl-hexane-2-one and 1,4-dichloro-4-methyl-3-(2,2,2-trichloroethyl)-pentan-2-one obtained from carbon tetrachloride and 1-chloro-3,3-dimethyl-pent-4en-2-one predominantly leads to cis-acids with bases (compare DE-OS (German Published Specification) 3,100,354 Example 4 and 5).

If, for example, 1,1,3,6-tetrachloro-4,4-dimethyl-1-hexen-5-one is used as the starting substance and aqueous sodium hydroxide solution is used as the base, the course of the reaction can be represented by the following equation:

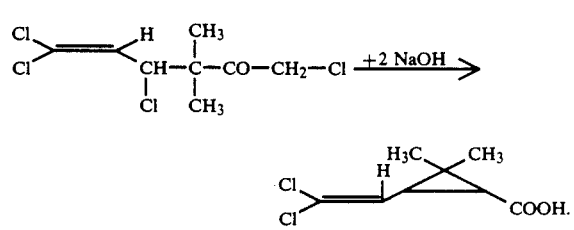

The general formula (II) provides a definition of the starting substances which can be used in this process.

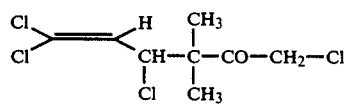

is used as the particularly preferred compound of the formula II.

The halogenoketones of the formula (II) used as starting substances are known in some cases and/or can be prepared by known processes in the generally customary manner (compare European Published Specification 095,047). Thus, for example, 1,1,3,6-tetrachloro-4,4-dimethyl-1-hexan-5-one can be prepared from 1,1,3-trichloro-4,4-dimethyl-1-hexan-5-one and chlorine.

In carrying out the process according to the invention, the starting substance of the formula (II) is taken in water and the aqueous alkali metal hydroxide solution (preferably sodium hydroxide solution or potassium hydroxide solution) is added dropwise.

In carrying out the process according to the invention, one mol of starting substance of the formula (I!) is reacted with 3 to 10 mol, preferably 3 to 5 mol, of alkali metal hydroxide solution.

Surprisingly, the reaction already takes place at room temperature or slightly elevated temperatures The reaction is in general carried out between 10° C. and 50° C., but preferably between 10° C. and 30° C. In particular, the reaction is carried out at room temperature.

The concentration of the aqueous alkali metal hydroxide solution can be between 0.5% and 20%, but preferably between 2.5% and 10% (the percentage data are percentages by weight).

Working up is carried out in the customary manner by generally known methods, for example by extraction of the reaction product in an organic water-immiscible solvent, drying of the extract and removal of the solvent.

The trans-permethric acid can be reacted as follows, for example, to give a pyrethroid end product with a potent insecticidal action:

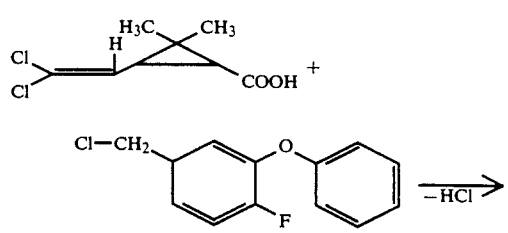

-continued

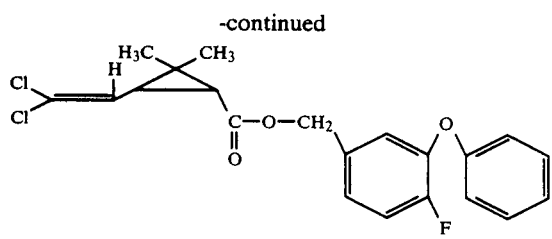

Preparation Examples

EXAMPLE 1

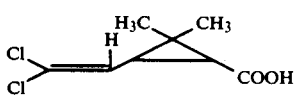

13.2 g of 1,1,3,6-tetrachloro-4,4-dimethyl-1-hexen-5-one (81% pure, about 0.04 mol) are taken in 75 ml of water. 7.5 g of sodium hydroxide, dissolved in 67.5 ml of water, are then added dropwise, without cooling and with stirring. The temperature thereby rises from 20° C. to about 26° C. The mixture is subsequently stirred for 12 hours, diluted with water and extracted three times with methylene chloride. The aqueous phase is acidified and extracted three times more with methylene chloride. The combined extracts of the (acid) extraction are dried and the solvent is removed. 7.0 g of trans-permethric acid (content: 97% according to gas chromatography, silylated) remain. This corresponds to a yield of 81.2% of theory.

EXAMPLE 2

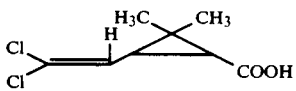

132 g of 1,1,3,6-tetrachloro-4,4-dimethyl-1-hexen-5-one (75% pure, about 0.375 mol) are taken in 1,050 ml of water and a solution of 105 g (1.875 mol) of potassium hydroxide in 945 ml of water is metered in at 25° C. The reaction is not exothermic. The mixture is subsequently stirred at 25°-27° C. for 6 hours and extracted three times with methylene chloride, and the aqueous phase is acidified and extracted three times more with methylene chloride. The combined extracts from the acid extraction are dried and the solvent is removed. 71 g of permethric acid remain (trans-content according to gas chromatography, silylated: 97%). This corresponds to a yield of 87.9% of theory).

Preparation of the starting substances:

EXAMPLE 3

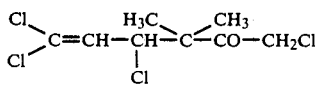

11.5 g (0.05 mol) of 1,1,3-trichloro-4,4-dimethyl1-hexen-5-one are dissolved in 50 ml of propio containing a little hydrogen chloride. 3.6 g (0.05 mol) of chlorine are then passed in at 0°-5° C. in the course of 15 minutes. The mixture is subsequently stirred at 0°-5° C. for a further 2 hours and the propionic acid is distilled off. The residue weighs 13.1 g and consists of 81% of 1,1,3,6-tetrachloro-4,4-dimethyl-1-hexen-5-one, 8% of starting substance and only 8.5% of dichloro-ketone. This corresponds to a yield of 80.4% of theory.

It will be appreciated that the instant specification and claims are set forth by way of illustration and not limitation, and that various modifications and changes may be made without departing from the spirit and scope of the present invention.

What is claimed is:

1. A process for the preparation of trans-2,2-dimethyl-3-(2,2-dichlorovinyl)-cyclopropane-carboxylic acid of the formula (I)

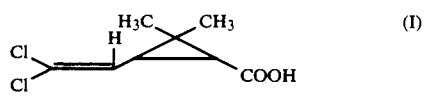

comprising reacting 1,1,3,6-tetrachloro-4,4-dimethyl-1-hexen-one at a temperature of 10° to 30° C.

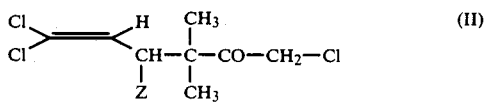

in which Z represents chlorine with an aqueous solution of an alkali metal hydroxide.

2. A process according to claim 1, wherein 3 to 10 mol of the alkali metal hydroxide are employed per mol of the 1,1,3,6-tetrachloro-4,4-dimethyl-1-hexen-one of the formula (II).

3. A process according to claim 1, wherein 3 to 5 mol of the alkali metal hydroxide are used per mol of 1,1,3,6-tetrachloro-4,4-dimethyl-1-hexen-one of the formula (II).

4. A process according to claim 1, wherein the alkali metal hydroxide is selected from the group consisting of NaOH and KOH.

5. A process according to claim 4, wherein the aqueous sodium hydroxide solution or potassium hydroxide solution used is present in a concentration of between 0.5 and 20 percent by weight.

6. A process according to claim 4, wherein the aqueous sodium hydroxide solution or potassium hydroxide solution used is present in a concentration of between 2.5 and 10 percent by weight.

* * * * *